(12) United States Patent
Hallberg et al.

(10) Patent No.: US 9,776,413 B2
(45) Date of Patent: Oct. 3, 2017

(54) METHOD AND SYSTEM FOR AUTOMATIC PREVENTIVE MAINTENANCE OF A NON-CONTACT PRINTING UNIT

(71) Applicant: SCA Hygiene Products AB, Göteborg (SE)

(72) Inventors: Patrik Hallberg, Västra Frölunda (SE); Anders Norder, Göteborg (SE); Sofia Richardson, Göteborg (SE); Lisa Palmqvist, Mölndal (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 15/306,839

(22) PCT Filed: Apr. 29, 2014

(86) PCT No.: PCT/SE2014/050529
§ 371 (c)(1),
(2) Date: Oct. 26, 2016

(87) PCT Pub. No.: WO2015/167374
PCT Pub. Date: Nov. 5, 2015

(65) Prior Publication Data
US 2017/0120595 A1 May 4, 2017

(51) Int. Cl.
*B41J 2/165* (2006.01)

(52) U.S. Cl.
CPC ...... *B41J 2/165* (2013.01); *B41J 2002/16573* (2013.01)

(58) Field of Classification Search
CPC B41J 2/165; B41J 2002/1657; B41J 2/16517; B41J 2/16535; B41J 2/16552; B41J 2/16505; B41J 2/16571; B41J 2/16511; B41J 2/16588; B41J 2/16508; B41J 2/16538; B41J 2/16544; B41J 2/1657
See application file for complete search history.

(56) References Cited

U.S. PATENT DOCUMENTS

| | | |
|---|---|---|
| 6,354,984 B1 | 3/2002 | Hensley et al. |
| 2004/0233241 A1 | 11/2004 | Salacz |
| 2005/0012768 A1 | 1/2005 | Thiessen et al. |
| 2005/0073548 A1 | 4/2005 | Suzuki |
| 2007/0206046 A1 | 9/2007 | Koike et al. |
| 2008/0088662 A1 | 4/2008 | Kojima |
| 2008/0218551 A1 | 9/2008 | Inaba |
| 2015/0097883 A1 | 4/2015 | Tamai et al. |

FOREIGN PATENT DOCUMENTS

| | | |
|---|---|---|
| JP | 2011-093222 A | 5/2011 |
| JP | 2015-074130 A | 4/2015 |

*Primary Examiner* — Juanita D Jackson
(74) *Attorney, Agent, or Firm* — Drinker Biddle & Reath LLP (57) ABSTRACT

A method for automatic preventive maintenance of a non-contact printing unit in a production line for absorbent articles such as diapers, sanitary napkins, panty liners, incontinence pads or similar is disclosed. The production line includes a plurality of production units including the non-contact printing unit. The method includes initiating automatic preventive cleaning of the non-contact printing unit upon production stop in the production line not caused by the non-contact printing unit. Also, a system arranged for initiating automatic preventive cleaning of a non-contact printing unit in a production line for absorbent articles is disclosed.

28 Claims, 6 Drawing Sheets

METHOD AND SYSTEM FOR AUTOMATIC PREVENTIVE MAINTENANCE OF A NON-CONTACT PRINTING UNIT

CROSS-REFERENCE TO PRIOR APPLICATION

This application is a §371 National Stage Application of PCT International Application No. PCT/SE2014/050529 filed Apr. 29, 2014, which is incorporated herein in its entirety.

TECHNICAL FIELD

The disclosure relates to a method and system for automatic preventive maintenance of a non-contact printing unit in a production line for absorbent articles such as diapers, sanitary napkins, panty liners, incontinence pads or similar.

BACKGROUND

A production line for producing absorbent articles such as hygiene articles includes a number of production units performing one or more production steps. One of these production units is the print unit, which may be a non-contact printing unit. The print unit can only print a certain number of articles or print for a certain period of time until the print unit is clogged by for instance ink or is contaminated by aerosols and has to be cleaned.

Cleaning the print unit requires that the production line is stopped or that all products produced during cleaning will be without print. This will have a negative impact on the machine efficiency.

There is thus a need for an improved method of cleaning the print unit.

SUMMARY

It is desired to provide a method and system for automatic preventive maintenance of a non-contact printing unit in a production line for absorbent articles where the previously mentioned problems are avoided or minimized. This can be achieved by the features described herein.

A method for automatic preventive maintenance of a non-contact printing unit in a production line for absorbent articles such as diapers, sanitary napkins, panty liners, incontinence pads or similar is disclosed. The production line includes a plurality of production units including the non-contact printing unit. The method includes: initiating automatic preventive cleaning of the non-contact printing unit upon production stop in the production line not caused by the non-contact printing unit.

A system for automatic preventive cleaning of a non-contact printing unit in a production line for absorbent articles such as diapers, sanitary napkins, panty liners, incontinence pads or similar is also disclosed. The production line includes a plurality of production units including the non-contact printing unit. The system is arranged to initiate automatic preventive cleaning of the non-contact printing unit upon production stop in the production line not caused by the non-contact printing unit.

During production of absorbent articles, the materials making up an absorbent article generally passes a number of production steps and quality controls. During each production step and quality control, a control system of the production line may initiate a production stop if for example a production step malfunctions, a production step is found to negatively affect the final quality of the absorbent article, or if a major machine error occurs such as a power cut or the like. One advantage of the methods and systems disclosed herein is that the non-contact printing unit can be preventively cleaned during a production stop which is not caused by the non-contact printing unit. The control system thus takes the opportunity of performing preventive cleaning of the printing unit when the production line is stopped although the printing unit functions properly merely for the reason of avoiding or at least postponing future production stops caused by a malfunctioning printing unit. The preventive cleaning reduces the need for stopping production due to that the non-contact printing unit malfunctions or requires a scheduled cleaning. This reduces unnecessary loss of production time and the amount of products discarded due to unacceptable printing quality.

Further advantages are achieved by implementing one or several of the particular features disclosed below. The method may for example include:
initiating the automatic preventive cleaning of the non-contact printing unit upon production stop caused by a production unit other than the non-contact printing unit.

Each production step can be performed by one or more production units. Each production unit may initiate a production stop if it malfunctions.

A control system of the production line may be arranged to control individual parts of the production line. A printer control unit may be arranged for controlling the printing unit and an associated printer cleaning device. The method can include:
initiating automatic preventive cleaning of the non-contact printing unit upon the printer control unit receiving a preventive cleaning instruction issued from the control system.

The method may further include:
communicating, after a terminated cleaning sequence, from the printer control unit to the control system, that the printing unit is ready for operation.

In certain embodiments, before the main production line can start production after automatic preventive cleaning has been initiated, the printer control unit must communicate to the control system that cleaning is finished. Otherwise, if production started before the cleaning procedure was complete, a number of absorbent products would not be printed or the non-contact printing unit could be damaged.

The method may further include:
initiating the automatic preventive cleaning of the non-contact printing unit upon each production stop in the production line not caused by the non-contact printing unit.

In order to ensure that the non-contact printing unit is kept in an operative state as much as possible the method may initiate cleaning every time the production line stops due to that a production unit other than the non-contact printing unit causes the production stop.

The method may further include:
evaluating the cause of the production stop;
taking the result of the production stop evaluation into account while deciding upon initiating the automatic preventive cleaning of the non-contact printing unit.

The step of evaluating the cause of the production stop may involve associating an estimated time duration with the production stop.

The control system may have a finite number of pre-defined production stop states, each of which is pre-classified in one of a plurality of different classes. The step of evaluating the cause of the production stop may include:
registering the production stop state; and checking the class associated with the registered production stop state, wherein the automatic preventive cleaning of the non-contact printing unit is initiated when the registered production stop state belongs to one or more predetermined classes.

Automatic preventive cleaning may be performed during each production stop in the production line not caused by the non-contact printing unit. Alternatively, if the cause of the production stop is evaluated and taken into account before automatic preventive cleaning is initiated, automatic preventive cleaning may only be performed if the estimated time duration of the production stop equals or exceeds the time duration of the automatic preventive cleaning. The evaluation of the production stop may, besides associating an estimated time duration with the production stop, also include registering a production stop state, checking the class associated with the registered production stop state and initiating the automatic preventive cleaning of the non-contact printing unit when the registered production stop state is associated with a predetermined class.

Classes may be associated with a gradually increasing estimated time duration for the production stop. This leads to that only certain classes have an estimated time duration associated with them which are of sufficient length so that the automatic preventive cleaning will be initiated.

The control system may generate a unique alarm signal for each production stop state. Each alarm signal may be pre-classified in one of a plurality of different classes. The step of evaluating the cause of the production stop may include:
  registering the alarm signal; and
  checking the class associated with the registered alarm signal,
wherein the automatic preventive cleaning of the non-contact printing unit is initiated when the registered alarm signal belongs to one or more predetermined classes.

The control system may include a cleaning urgency index representing the cleaning urgency of the printing unit. The method can include:
  monitoring the cleaning urgency index; and
  taking the result of both the production stop evaluation and current cleaning urgency index into account while deciding upon initiating the automatic preventive cleaning of the non-contact printing unit.

The cleaning urgency index may be a function of one or more of: time period since previous printing unit cleaning event; printing unit still stand time period; ink flow resistance in printer nozzle; accumulated length of sheet material of the absorbent article having passed the printing unit; and accumulated printing volume. The ink flow resistance in the printer nozzle may for example be determined by measuring the flow resistance in a flow passage between ink pumping means and ink outlet hole.

Instances may arise when the production line does not experience any production stops at all or any production stops of a sufficient length for an extended period of time. This means that the non-contact printing unit has not experienced any preventive cleaning during that time period. In this case, the cleaning urgency index may need to be taken into account when a production stop occurs. If it is deemed necessary by the cleaning urgency index that cleaning of the non-contact printing unit must take place, taking the cleaning urgency index into account may result in that the non-contact printing unit is cleaned during a production stop which normally would be too short for automatic preventive cleaning to take place.

The relative position of a printing nozzle of the printing unit and an opposing support surface for the object to be printed may be adjusted prior to performing the preventive cleaning for enabling access to the printer nozzle, wherein the relative position is adjusted by one or more of: raising the printer nozzle away from the opposing support surface; lowering the opposing support surface away from the printer nozzle; and moving the printing nozzle sideways.

The production stop may be an unplanned production stop. Unplanned production stop may for example be caused by a sudden malfunctioning in a production step or unplanned production stop initiated by a human operator running the production line, such as an emergency stop. Planned production stop is for example a stop initiated for planned maintenance work or the like, and where the control system was informed of the planned production stop in advance for being able to plan its operation while taking the planned production stop into account.

The method may also include:
  initiating additional automatic cleaning of the non-contact printing unit after a predetermined period of time has passed since the last cleaning. This procedure ensures that required preventive cleaning of the printing unit is performed at regular intervals even if no production stops occur.

The method may further include:
  initiating additional automatic cleaning of the non-contact printing unit upon the non-contact printing unit providing an error signal to the production line control system.

The system for automatic preventive cleaning can involve corresponding features and advantages as disclosed in relation with the method described above and below.

BRIEF DESCRIPTION OF THE DRAWINGS

Examples in accordance with embodiments of the invention are illustrated in the figures as briefly described below.

DETAILED DESCRIPTION OF PARTICULAR EMBODIMENTS

Figure 1:
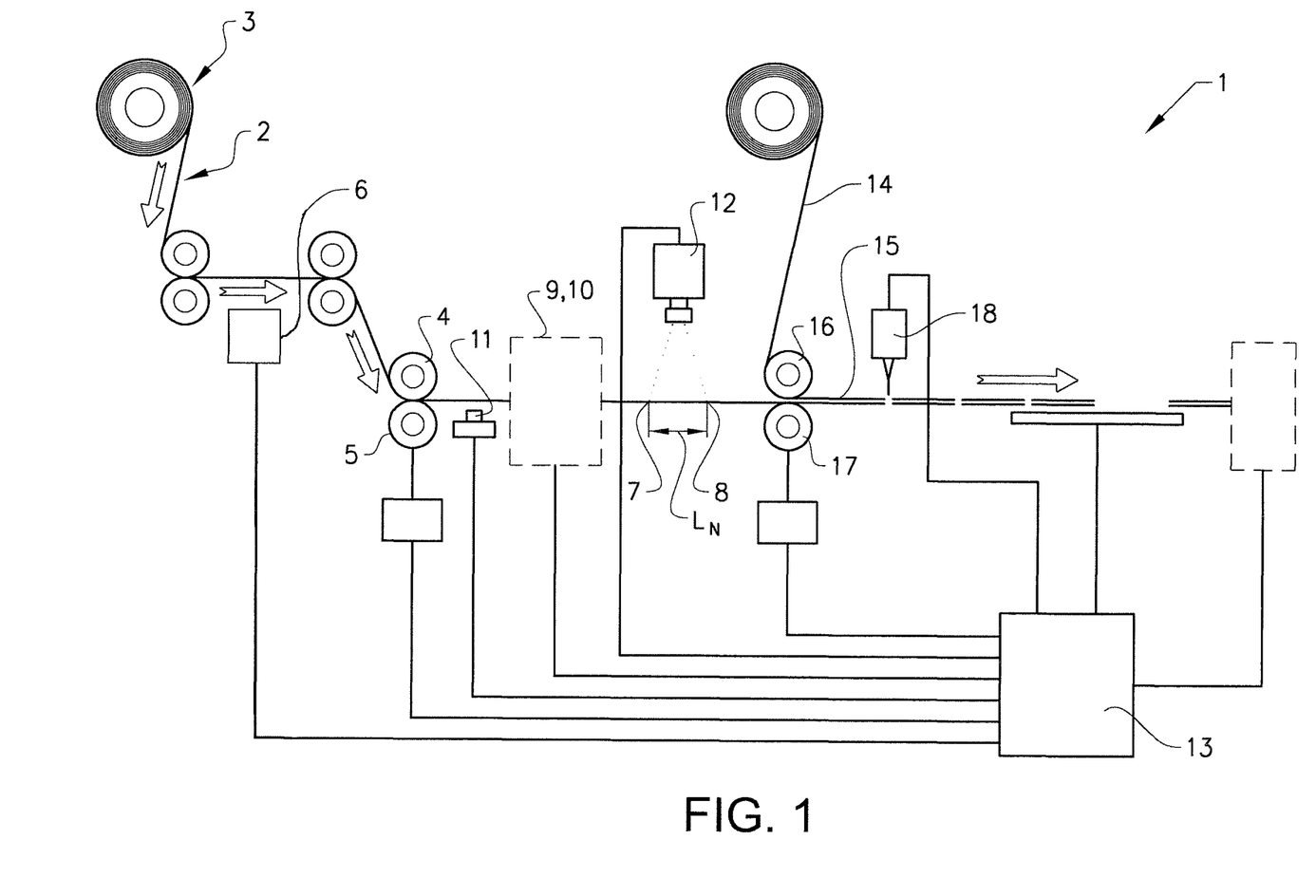
FIG. 1 schematically discloses a production line according to an embodiment.

FIG. 1 is a schematic and simplified view of a production line 1 for manufacturing absorbent products. More specifically, the production line 1 is arranged for manufacturing absorbent products that start out as an essentially continuous first material web 2, which is fed forward in a known way from a first roll 3 or the like, in a direction that is indicated by arrows in FIG. 1.

According to an example, the first material web 2 consists of a back sheet for a disposable diaper, that is, a material of the type that is non-permeable to liquid or that has at least a high resistance to the penetration of liquid, but which, however, is breathable. For this purpose, the first material web 2 includes a thin and waterproof plastic film of, for example, polyethylene, polypropylene or polyester. Alternatively, a laminate of non-woven material and plastic film or other suitable and previously-known layers of material can be utilized as a liquid-tight back sheet.

The first material web 2 can be fed forward by means of two rollers 4, 5 which are arranged to give the first material web 2 that will become the back sheet, a certain given feed speed.

FIG. 1 also shows a non-contact printing unit 6 arranged to print a motif on the back sheet. This motif is, in the present example, printed on the first material web 2 as a first production step. The non-contact printing unit 6 can however be set-up at any position along the length of the production line 1 in order to print a motif on any part of the absorbent article.

As shown in FIG. 1, the first material web 2 can be divided into a certain nominal division length LN, which is a length that is defined between two transverse positions 7, 8 that delimit a particular product. According to the embodiment that is shown in FIG. 1, the nominal division length LN includes a product length that corresponds to the front edge and rear edge of a finished product. However, these lines are not printed on the first material web 2.

As shown in FIG. 1 in a schematic and simplified way, the first material web 2 is fed through processing equipment 9 where a number of work elements and process steps are carried out by a number of production units 10. These work elements can include, for example, the application of various types of absorbent material, wadding material and the like, and any other material and components such as, for example, elastic, adhesive tape and the like. The work elements that are carried out in the processing equipment 9 can also include folding, cutting, ultrasound welding and other processing steps. The manufacture of absorbent products by means of a series of such work elements is already known, and for this reason will not be described here in detail. As an example, however, reference can be made to patent document WO 00/59429 that describes an example of a previously-known manufacturing process for absorbent products.

Still with reference to FIG. 1, it can be noted that the first material web 2 has passed a detecting device 11 just before it is fed into the processing equipment 9. The detecting device 11 is arranged to detect any production errors or quality deficiencies in the absorbent article. In addition, the first material web 2 is fed past a gluing station 12 at which adhesive is applied in order to enable a subsequent outer layer to be glued on, in the way that will be described below.

In FIG. 1, detecting device 11 can include a suitable device for optical inspection, according to one example in the form of a video camera that is arranged in association with the first material web 2. The detecting device 11 may also include a suitable device for inspection by other means, for instance infrared, x-ray, laser or the like.

In addition, in FIG. 1, the detecting device 11 is connected to a computer-based control system 13. Information from the detecting device 11 is transmitted in this way to the control system 13, which in turn is provided with software for image processing that is arranged to detect production errors or quality deficiencies. In addition, the control system 13 is connected to the production units 10 of processing equipment 9.

In FIG. 1, when the first material web 2 has been fed past the detecting device 11, it meets a second material web 14, in the form of an essentially liquid-permeable layer that is intended to form an outer layer of the finished product. For this reason, the second material web 14 can include a non-woven material with a soft and smooth surface, such as, for example, a spun bond material of polypropylene fibre. Other examples of materials that are suitable for constituting the outer layer are perforated plastic films, such as, for example, a perforated polyester film.

In FIG. 1, the second material web 14 is thus joined to the first material web 2 (together with any additional layers of material and other components that are added in association with the processing equipment 9 as described above) for example by means of the adhesive that was previously applied at the gluing station 12. In this way, a complete material web 15 is created, intended to define a number of manufactured products, which is fed forward in a direction that is indicated by an arrow in FIG. 1 and taken up and fed forward by means of two additional driving units, for example in the form of two rotating feeding rollers 16, 17 arranged respectively over and under the complete material web 15. In this way, the complete material web 15 can be fed forward.

After the assembly with the second material web 14, a complete continuous material web 15 is thus created, including a number of finished absorbent products that are still joined together. This material web 15 is finally fed past a cutting station 18, suitably of the "cross-cutter" type, where cutting is carried out at positions that essentially correspond to the transverse positions 7, 8 for each finished product. In this way, a number of finished products are created in the form of absorbent products.

The above description is of course also applicable to other types of absorbent articles, such as sanitary napkins, panty liners, incontinence pads or similar.

Figure 2:
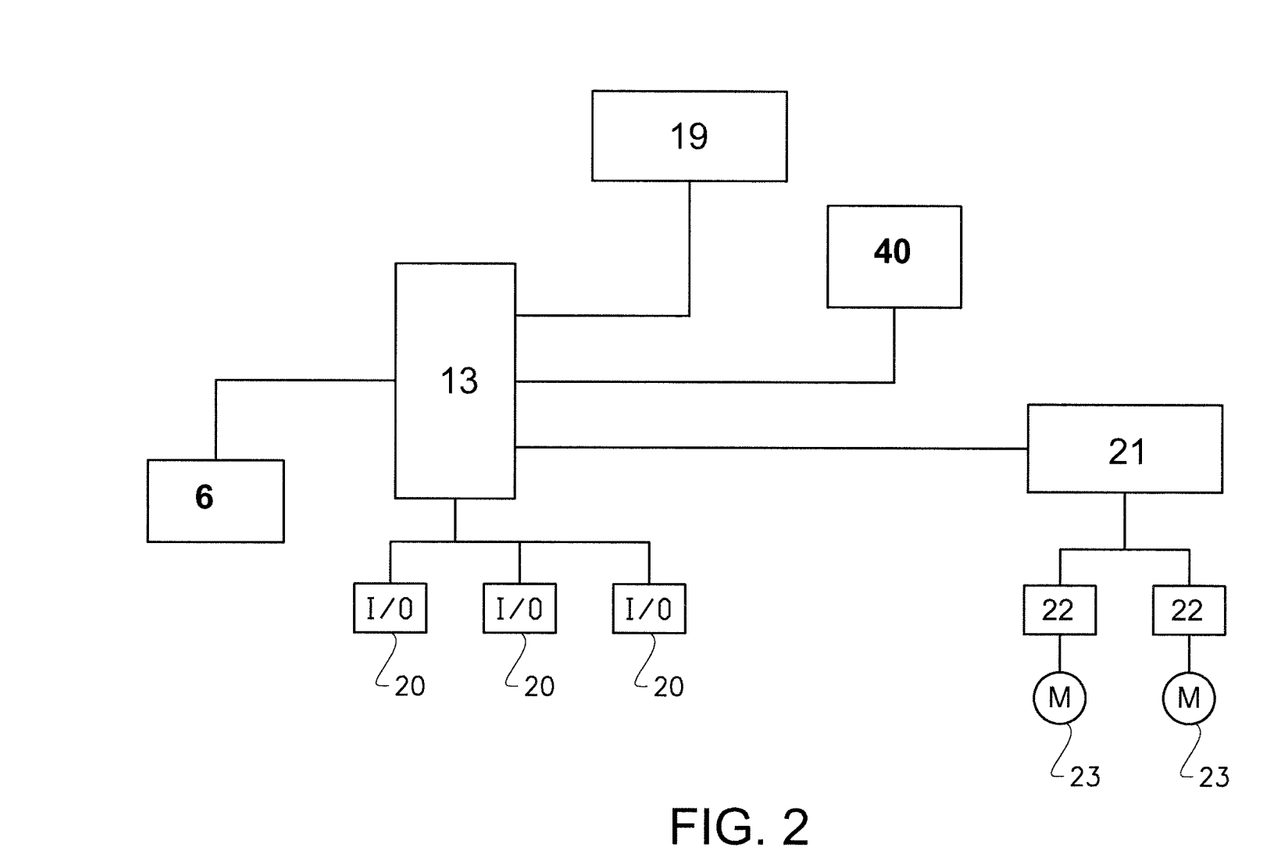
FIG. 2 schematically shows a control system setup for a system according to an embodiment.

FIG. 2 schematically shows a setup for a control system 13 for a production line 1. The control system 13 includes a main programmable logic controller (PLC) having a human-machine-interface (HMI) 19. The HMI 19 is used by operators of the production line 1 to set various control parameters in order to control the process of manufacturing the absorbent articles and to receive visual or aural statuses, alerts and alarms etc. The main PLC can be connected to a number of input/outputs (I/Os) 20. The I/Os 20 can for instance be various sensors, circuit breakers, solenoid valves and other process related equipment associated with various production units 10. The I/Os 20 can provide the main PLC with for instance sensor data and operative state of circuit breakers and solenoid valves. With operative state is meant for instance on/off or different positions. The I/Os 20 can further provide the main PLC with information regarding the operational state of each piece of equipment connected to an I/O 20. If the operational state of a piece of equipment changes from operating to non-operating, the main PLC is alerted. Depending on the type of error the main PLC may stop the production line 1. The main PLC can further be connected to a motor controller (MC) 21 which in turn is connected to motor drives (D) 22 which control the various motors (M) 23 of the production line 1. The motor controller 21 ensures that the motors 23 are synchronized over the production line 1 to ensure that proper speeds of the material webs 2, 14, 15 are achieved. The motors 23 in FIG. 2 may for instance drive rollers 4, 5 in FIG. 1.

In FIG. 2, the main PLC is connected to the non-contact printing unit 6. According to an embodiment, a printer control unit is arranged for controlling the non-contact printing unit and an associated printer cleaning device. The printer control unit typically includes one or more PLCs having I/Os for controlling components of the printing unit and the cleaning device. Components of the printing unit typically include a printing nozzle and components of the cleaning device typically include actuators for moving the printing nozzle, material web or cleaning unit. The printer control unit may communicate with the main PLC by means of a bus system, serial communication or any other signal communication system. The main PLC may typically provide the printer control unit with information about what, when, and where to print, and the printer control unit typically provides feed-back concerning printing unit status and alarm signals. The main PLC can also be connected to one or more additional distributed PLCs 40 controlling other parts of the production line. In particular embodiments, a distributed PLC is more independent than an I/O or a motor drive and includes its own control programming and only sends and/or receives information, instructions and/or statuses from and to the main PLC.

Depending on the complexity of the control system, a less hierarchical control system may be desirable where components of the printing unit and the cleaning device are controlled directly by the main PLC via its I/Os. Still more alternatively, some components of the printing unit and the cleaning device may be controlled by the main PLC and other parts by one or more sub PLCs associated with the printing unit or cleaning device.

Figure 3A:
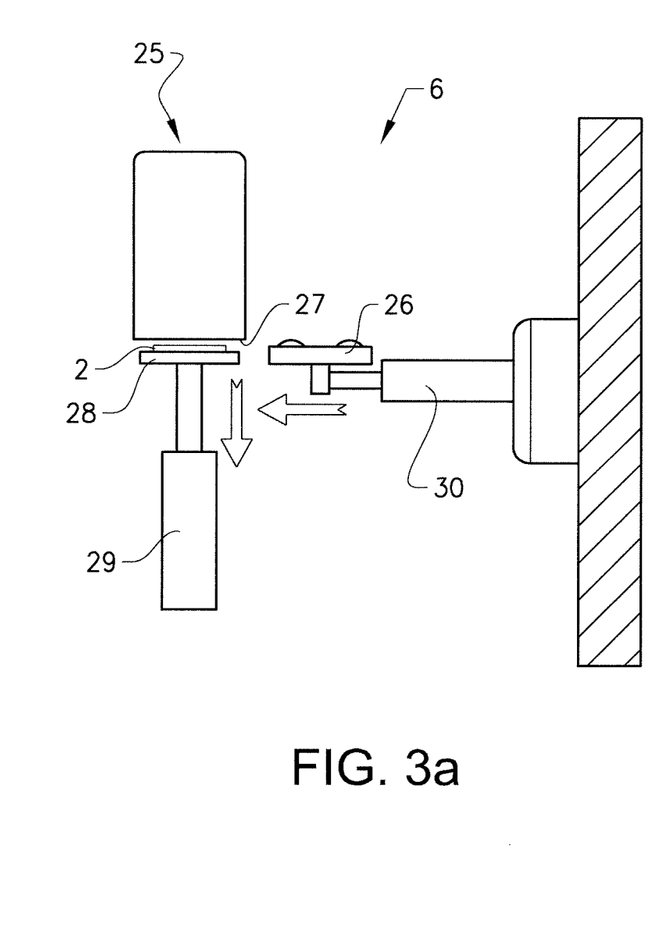
FIGS. 3a-b schematically discloses a print unit according to an embodiment.
Figure 3B:
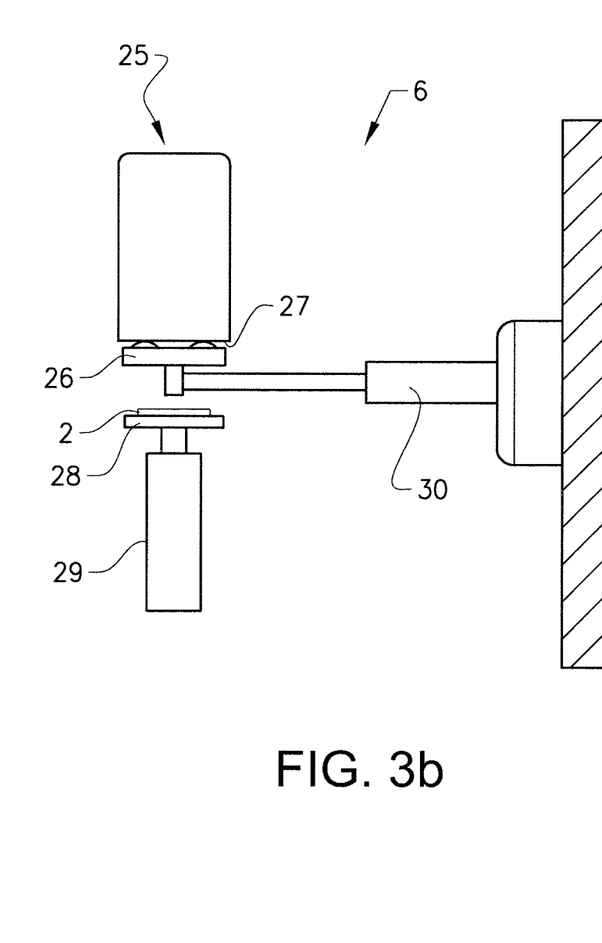

FIGS. 3a and 3b schematically illustrate a non-contact printing unit 6. The non-contact printing unit 6 includes a print unit 25 with at least one printing nozzle 27, and a cleaning device includes a cleaning unit 26 and actuating cylinders 29, 30. The non-contact printing unit 6 and the cleaning device may be provided as one integral unit or as two separate units. The print unit 25 is situated above an opposing support surface 28 on which the material web 2 runs. According to the embodiment illustrated in FIGS. 3a and 3b, the adjustment of the relative position of the printing nozzle 27 of the non-contact printing unit 6 and the opposing support surface 28 for the object to be printed is performed as follows. As shown in FIG. 3a, the opposing support surface 28 is placed on top of a first cylinder 29 which is arranged to be lowered upon a production stop in the production line 1. The cleaning unit 26 is located on a second cylinder 30 which is arranged to extend and place the cleaning unit 26 in a cleaning position upon a production stop in the production line 1. The movement of the cylinders are indicated by arrows. In the cleaning position, the at least one printing nozzle 27 of the non-contact printing unit 6 can be cleaned by the cleaning unit 26. Upon a production stop in the production line 1, the opposing support surface 28 and thereby the material web 2 is lowered, thereby creating a space between the print unit 25 and the opposing support surface 28. This allows the cleaning unit 26 to extend to the cleaning position into the space between the print unit 25 and the opposing support surface 28. This is shown in FIG. 3b. After cleaning is complete or terminated before completion, the second cylinder 30 is controlled to be retracted, thereby removing the cleaning unit 26 from the cleaning position, and the first cylinder 29 is controlled to raise the opposing support surface 28 and material web 2, returning the print unit 25 to its original state. Manufacturing can thereafter be resumed.

Figure 4A:
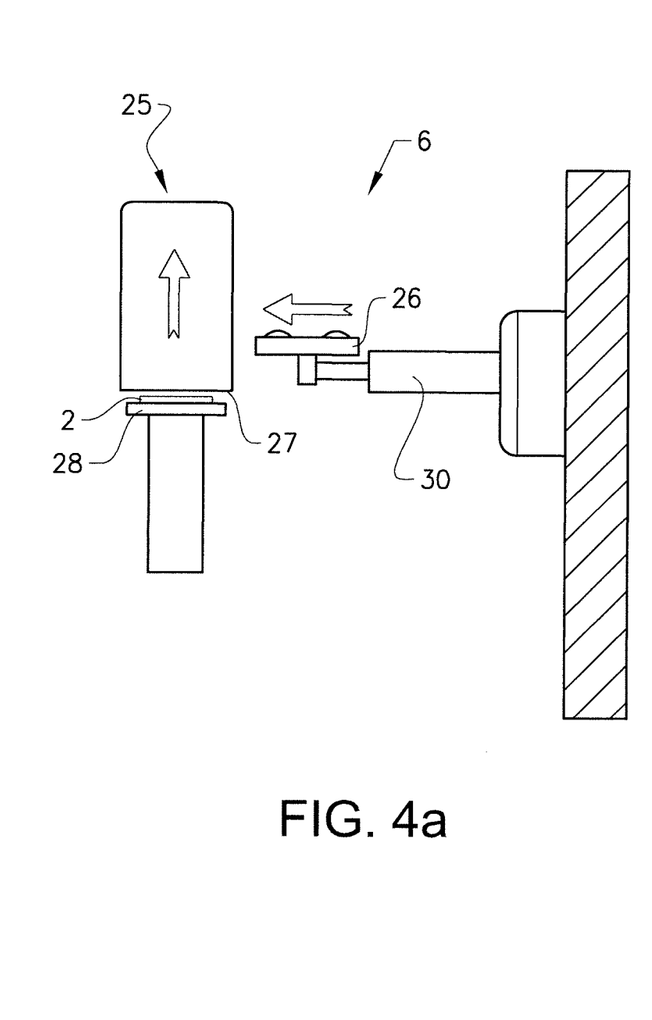
FIGS. 4a-b schematically discloses a print unit according to an embodiment.
Figure 4B:
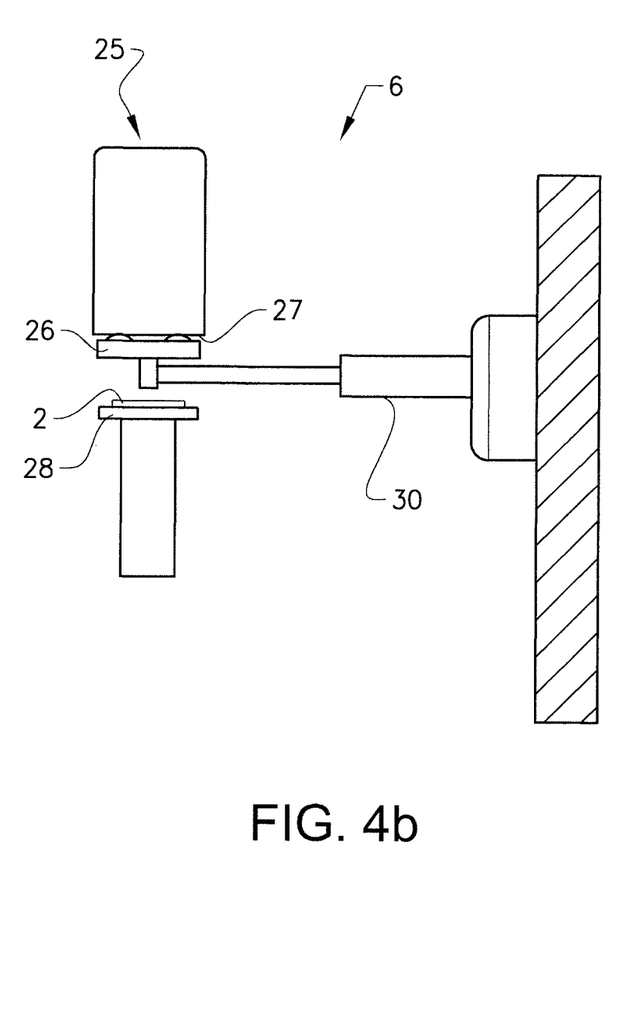

FIGS. 4a and 4b schematically illustrate an alternative non-contact printing unit 6 and cleaning device. According to the embodiment illustrated in FIGS. 4a and 4b, the adjustment of the relative position of the printing nozzle 27 of the non-contact printing unit 6 and the opposing support surface 28 for the object to be printed is performed as follows. As is shown in FIG. 4a, the print unit 25 is controlled to be raised upon a decision to perform cleaning of the print unit 25. The cleaning unit 26 is located on a second cylinder 30 as described in conjunction with FIG. 3a. Upon decision to perform cleaning the print unit 25 is raised away from the opposing support surface 28, thereby creating a space between the print unit 25 and the opposing support surface 28. This allows the cleaning unit 26 to extend to the cleaning position into the space between the print unit 25 and the opposing support surface 28. This is shown in FIG. 4b. After cleaning is complete or terminated before completion, the second cylinder 30 is controlled to retract, thereby removing the cleaning unit 26 from the cleaning position, and the print unit 25 is controlled to be lowered towards the opposing support surface 28 and material web, returning the print unit 25 to its original state. Manufacturing can thereafter be resumed.

Figure 5A:
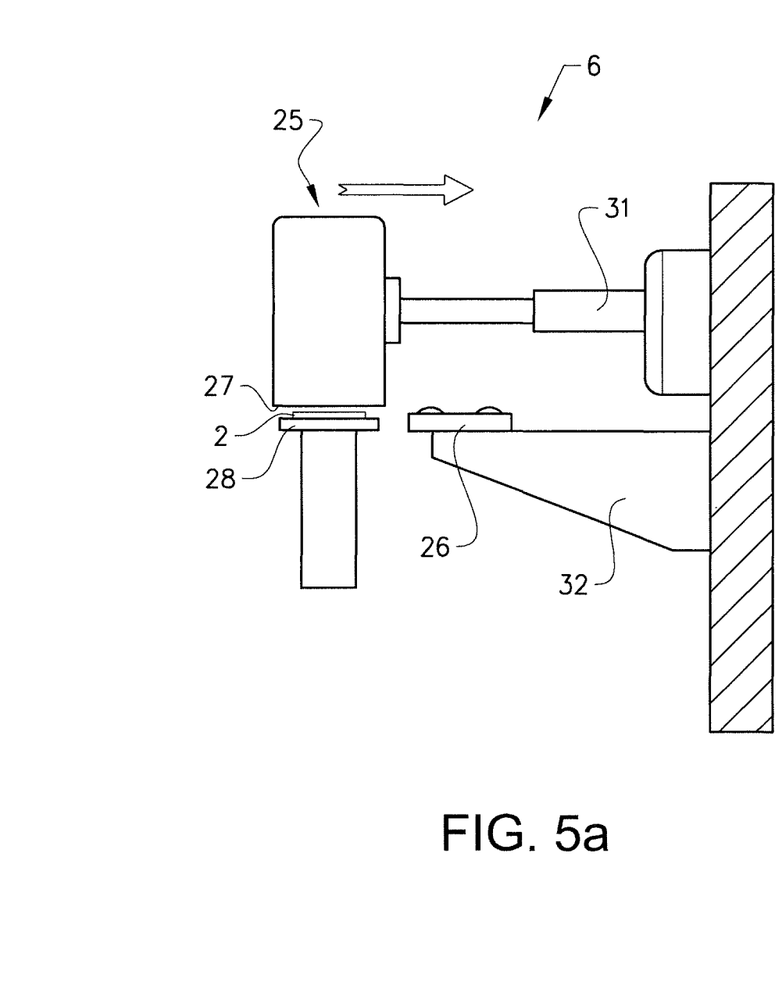
FIGS. 5a-b schematically discloses a print unit according to an embodiment.
Figure 5B:
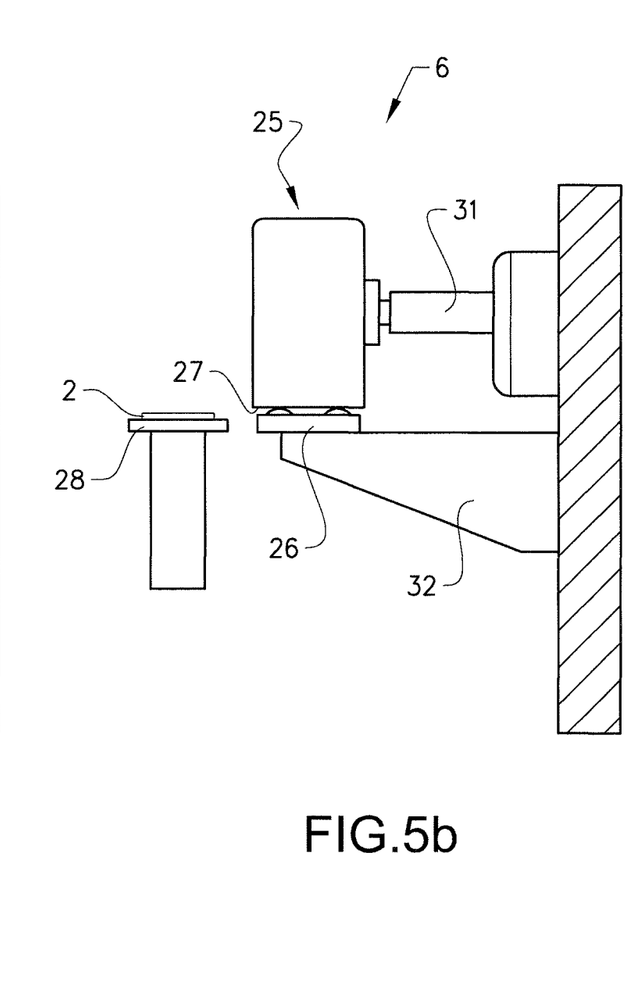

FIGS. 5a and 5b schematically illustrate an alternative print unit 25, and an alternative non-contact printing unit 6. According to the embodiment illustrated in FIGS. 5a and 5b, the adjustment of the relative position of the printing nozzle 27 of the non-contact printing unit 6 and the opposing support surface 28 for the object to be printed is performed as follows. As shown in FIG. 5a, the print unit 25 is attached to a third cylinder 31 which in this aspect is arranged to move at least the printing nozzle 27 of the print unit 25 sideways upon decision to perform cleaning of the print unit 25. The cleaning unit 26 in this aspect is located on a fixed position 32. Upon decision to perform cleaning, the print unit 25 is moved sideways away from the opposing support surface 28. The print unit 25 is moved to a cleaning position on top of the cleaning unit 26 as shown in FIG. 5b. The cleaning unit 26 may alternatively be attached to a second cylinder 30 as described in conjunction with FIG. 3a. In this case, both the print unit 25 and the cleaning unit 26 can move from their respective initial positions, thereby reaching a cleaning position. After cleaning is complete or terminated before completion, the printer control unit retracts the second cylinder 30, thereby removing the cleaning unit 26 from the cleaning position and moves the print unit 25 back towards the opposing support surface 28 and material web 2. Manufacturing can thereafter be resumed.

Figure 6:
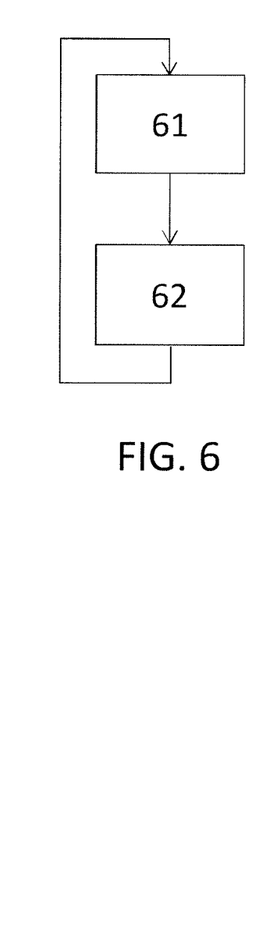
FIG. 6 shows an embodiment of the method.

Method steps in accordance with embodiments of the invention will be described more in detail with respect to FIGS. 6-10, which show different embodiments of the method. FIG. 6 discloses the core steps of an embodiment. The first step 61 involves identifying a production stop in the production line, as well as the cause of the production stop. Production stops are generally decided by the main PLC upon receiving an alarm signal from any of the distributed PLCs 40 or when information from the I/O ports 20 of the main PLC indicates malfunctioning for any reason. The cause for the production stop may be identified based on the type of alarm signal the main PLC received. Each PLC may be programmed as a finite state machine having a specific state for each possible operation mode. When a malfunction of any kind is detected in any of the distributed PLSs 40 the control system of that PLC enters a specific state predefined for this situation, and a corresponding alarm is transmitted to the main PLC. Depending on the type of alarm received, the main PLC decides to stop the production line completely or partly, slow down the production line, or the like until the problem is eliminated. The main PLC may thus, for example, determine the cause of a production stop based in the specific alarm received. Alternatively, if no alarm system or finite state machine system is used, some other means for determining the cause or origin of the production stop may be used. After having determined the cause of the production stop, and having determined that the production stop was not caused by the non-contact printing unit, preventive cleaning is initiated in step 62.

The preventive cleaning may be performed by a control unit dedicated to the printing unit 6 and/or cleaning device upon receiving an instruction from the main PLC to initiate the cleaning procedure. Alternatively, in case the main PLC itself controls the cleaning device the cleaning process may be initiated without further communication.

Figure 7:
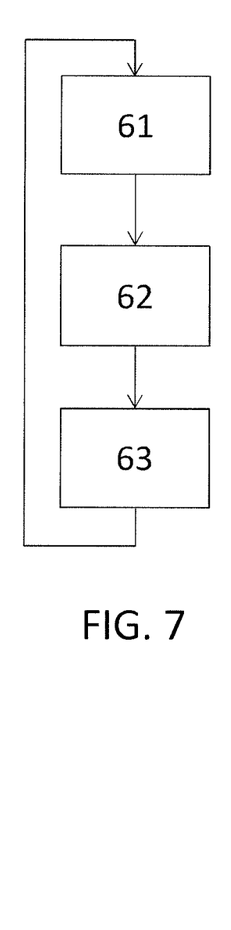
FIG. 7 shows an embodiment of the method.
Figure 8:
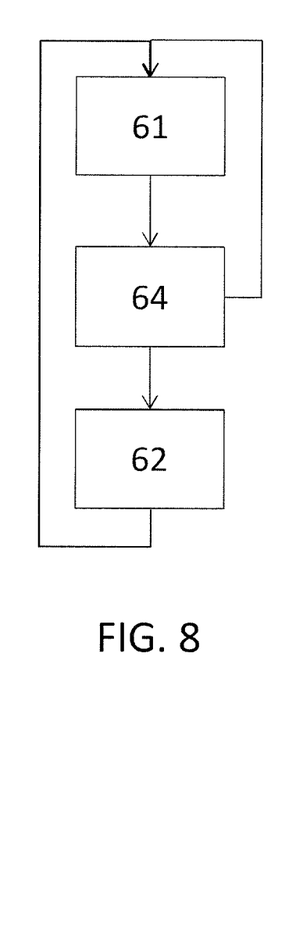
FIG. 8 shows an embodiment of the method.

FIG. 7 illustrates a method similar to FIG. 6 but with the additional final step 63 of communicating, after terminated cleaning sequence, from the printer control unit to the control system, that the printing unit is ready for operation. Such a feedback information is useful to avoid that the production is started before the cleaning process has finished.

According to an embodiment, automatic preventive cleaning of the non-contact printing unit 6 may be initiated upon each production stop in the production line 1 not caused by the non-contact printing unit 6. This approach is straightforward and requires less evaluation. However, for avoiding that the cleaning process is initiated although the production stop is very short, e.g. shorter than the cleaning process, a more complex method may be required. According to a further embodiment schematically shown in FIG. 8, the step 61 of identifying and evaluating the cause of production stop is followed by a step 64 of taking the result of the production stop evaluation into account while deciding upon initiating the automatic preventive cleaning of the non-contact printing unit. Typically, the step 64 of evaluating the cause of the production stop involves associating an estimated time duration with the production stop. In case it is determined that preventive cleaning should be initiated, the method enters step 62 for performing the cleaning. Otherwise, the method skips the cleaning process. This may, for example, occur when the production stop was evaluated to be relatively short.

Figure 9:
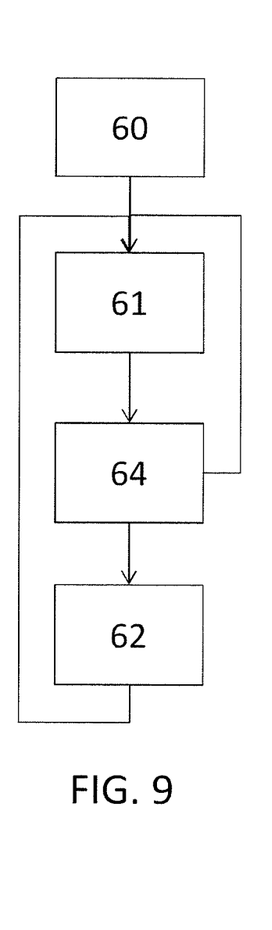
FIG. 9 shows an embodiment of the method.

One practical solution for performing the mentioned evaluation is shown with reference to FIG. 9 and involves a first step 60 of initial classification of possible production stops, where all production stop states are first associated with an individual production stop time duration and subsequently classified in one of at least two classes. The classes can be associated with a gradually increasing estimated time duration for the production stop. In the subsequent evaluation step 64, the control system may quickly check the class associated with the registered production stop state and based in the classification rules used in the initial classification step 60. For example, two classes are available, one class associated with production stop states normally taking longer time than an average cleaning process, and the other class associated with production stop states normally taking less time than an average cleaning process. If it is determined during the evaluations step 64 that the present production stop state belongs to the first class (predetermined class), cleaning is immediately initiated without further investigation of the underlying cause for the production stop.

Figure 10:
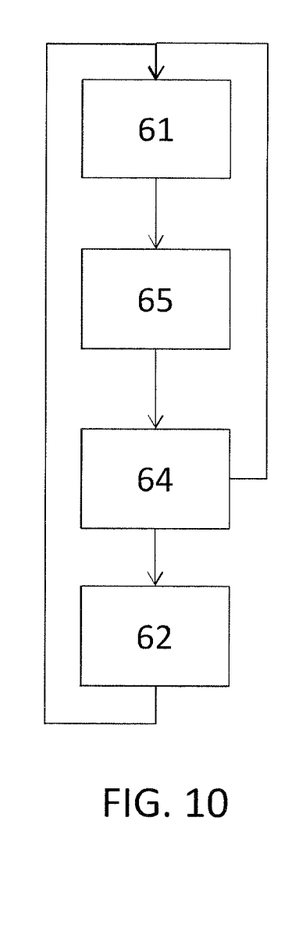
FIG. 10 shows an embodiment of the method.

Yet another embodiment method is disclosed with reference to FIG. 10. This embodiment involves the step 61 of identifying a production stop in the production line, as well as the cause of the production stop. Thereafter, the method involves the step 65 of determining a status of a present cleaning urgency index. The cleaning urgency index is used for preventing that a preventive cleaning of the printing unit is initiated very shortly after a previous preventive cleaning event, simply to because the need for additional preventive cleaning might be very low and the risk for additional production delays caused by the preventive cleaning event itself is not insignificant. For example, in case the leaning urgency index is low, i.e. there exists a low demand for cleaning, and the estimated production stop time period is about the same or shorter than the estimated time needed for performing the cleaning session, then the method and system may be better off not initiating the automatic preventive cleaning. However, in a situation where the cleaning urgency index is high, and the estimated production stop time period is about the same or shorter than the estimated time need for performing the cleaning session, then the method and system is likely better off initiating the automatic preventive cleaning in order to avoid an additional production stop in the near future caused by malfunction of the printing unit, despite the fact that the present production stop may be slightly prolonged due the preventive cleaning. The cleaning urgency index may thus assist the control system to take better and more long-term decisions. The cleaning urgency index can be continuously monitored by the control system. The cleaning urgency index may be a function of many different aspects, for example a time period since previous printing unit cleaning event. The printing unit may be assumed to become increasingly clogged and dirty with time, in particular production time, such that the time period that has passed since the previous cleaning event may be a relevant aspect. Another relevant aspect may be printing unit still stand time period, such as still stand time period since last printing operation. Ink dries over time and may cause printing problems. Printing still stand time may thus be a relevant aspect. Still another relevant aspect may be ink flow resistance in printing nozzle. This may, for example, be determined by monitoring flow resistance in flow passage between pumping means and ink outlet hole, which may be measured by analysing pumping means power requirement. Still further relevant aspects may be accumulated length of sheet material having passed the printing unit since the previous cleaning session, or accumulated printing volume since last cleaning session, for example quantified in terms of consumed accumulated ink volume.

Thereafter the method involves the step 64 of deciding upon initiating the automatic preventive cleaning of the non-contact printing unit while taking the result of both the production stop evaluation and current cleaning urgency index into account. In case it is determined that preventive cleaning should be initiated, the method enters step 62 for performing the cleaning. Otherwise the method skips the cleaning process.

Reference signs mentioned in the claims should not be seen as limiting the extent of the matter protected by the claims, and their sole function is to make claims easier to understand.

As will be realised, embodiments of the invention are capable of modification in various obvious respects, all without departing from the scope of the appended claims. Accordingly, the drawings and the description are to be regarded as illustrative in nature, and not restrictive.

The invention claimed is:

1. A method for automatic preventive maintenance of a non-contact printing unit in a production line for absorbent articles, wherein the production line comprises a plurality of production units including the non-contact printing unit the method comprising:

initiating automatic preventive cleaning of the non-contact printing unit upon production stop in the production line not caused by the non-contact printing unit, initiating additional automatic cleaning of the non-contact printing unit after a predetermined period of time has passed since the last cleaning, wherein the relative position of a printing nozzle of the printing unit and an opposing support surface for the object to be printed is adjusted prior to performing the preventive cleaning for enabling access to the printer nozzle, wherein the relative position is adjusted by one or more of: raising the printer nozzle away from the opposing support surface; lowering the opposing support surface away from the printer nozzle; and moving the printing nozzle sideways.

2. The method according to claim 1, wherein the initiating of the automatic preventive cleaning of the non-contact printing unit is upon production stop caused by a production unit other than the non-contact printing unit.

3. The method according to claim 1, wherein a control system of the production line is arranged to control individual parts of the production line, wherein a printer control unit is arranged for controlling the non-contact printing unit and an associated printer cleaning device, and wherein the initiating of the automatic preventive cleaning of the non-contact printing unit upon the printer control unit receives a preventive cleaning instruction issued from the control system.

4. The method according to claim 3, further comprising communicating, after terminated cleaning sequence, from the printer control unit to the control system, that the printing unit is ready for operation.

5. The method according to claim 1, wherein the initiating of the automatic preventive cleaning of the non-contact printing unit is upon each production stop in the production line not caused by the non-contact printing unit.

6. The method according to claim 1, wherein the method comprising:

evaluating the cause of the production stop; and taking the result of the production stop evaluation into account while deciding upon initiating the automatic preventive cleaning of the non-contact printing unit.

7. The method according to claim 6, wherein the step of evaluating the cause of the production stop involves associating an estimated time duration with the production stop.

8. The method according to claim 6, wherein a control system of the production line has a finite number of pre-defined production stop states, each of which being pre-classified in one of a plurality of different classes, the step of evaluating the cause of the production stop comprising:

registering the production stop state; and checking the class associated with the registered production stop state, wherein the initiating of the automatic preventive cleaning of the non-contact printing unit occurs when the registered production stop state belongs to one or more predetermined classes.

9. The method according to claim 8, wherein the classes are associated with a gradually increasing estimated time duration for the production stop.

10. The method according to claim 6, wherein a control system generates a unique alarm signal for each production stop state, each alarm signal being pre-classified in one of a plurality of different classes, wherein the step of evaluating the cause of the production stop comprises:

registering the alarm signal; and checking the class associated with the registered alarm signal, wherein the initiating of the automatic preventive cleaning of the non-contact printing unit occurs when the registered alarm signal belongs to one or more predetermined classes.

11. The method according to claim 6, wherein a control system comprises a cleaning urgency index representing the cleaning urgency of the printing unit, and the method further comprises:

monitoring the cleaning urgency index; and taking the result of both the production stop evaluation and current cleaning urgency index into account while deciding upon initiating the automatic preventive cleaning of the non-contact printing unit.

12. The method according to claim 11, wherein the cleaning urgency index is a function of one or more of: time period since previous printing unit cleaning event; printing unit still stand time period; ink flow resistance in printing nozzle; accumulated length of sheet material of the absorbent article having passed the printing unit; and accumulated printing volume.

13. The method according to claim 1, wherein the production stop is an unplanned production stop.

14. The method according to claim 1, further comprising:

initiating additional automatic cleaning of the non-contact printing unit upon the non-contact printing unit providing an error signal to a production line control system.

15. A system for automatic preventive cleaning of a non-contact printing unit in a production line for absorbent articles, the system comprising: a print unit with a printing nozzle, and an opposing support surface for guiding an object to be printed, wherein the production line comprises a plurality of production units including the non-contact printing unit, wherein the system is arranged for initiating automatic preventive cleaning of the non-contact printing unit upon production stop in the production line not caused by the non-contact printing unit, wherein the system is arranged for initiating additional automatic cleaning of the non-contact printing unit after a predetermined period of time has passed since the last cleaning, wherein a relative position of the printing nozzle and the opposing support surface is arranged to be adjusted prior to performing the preventive cleaning for enabling access to the printer nozzle, and wherein the relative position of the printing nozzle and the opposing support surface is adjusted by one or more of: raising the printer nozzle away from the opposing support surface; lowering the opposing support surface away from the printer nozzle; and moving the printing nozzle sideways.

16. The system according to claim 15, wherein the system is arranged for initiating the automatic preventive cleaning of the non-contact printing unit upon production stop caused by a production unit other than the non-contact printing unit.

17. The system according to claim 15, further comprising a control system, a printer control unit and a printer cleaning device, wherein the control system of the production line is arranged to control individual parts of the production line, wherein the printer control unit is arranged for controlling the non-contact printing unit and the associated printer cleaning device, and wherein the system is arranged for initiating automatic preventive cleaning of the non-contact printing unit upon the printer control unit receiving a preventive cleaning instruction issued from the control system.

18. The system according to claim 17, wherein the printer control unit, after terminated cleaning sequence, confirms to the control system that the printing unit is ready for operation.

19. The system according to claim 15, wherein the system is arranged for initiating automatic preventive cleaning of the non-contact printing unit upon each production stop in the production line not caused by the non-contact printing unit.

20. The system according to claim 15, wherein the system is arranged for evaluating the cause of the production stop, and taking the result of the production stop evaluation into account while deciding upon initiating the automatic preventive cleaning of the non-contact printing unit.

21. The system according to claim 20, wherein evaluation of the cause of the production stop involves associating an estimated time duration with the production stop.

22. The system according to claim 20, further comprising a control system, wherein the control system is arranged to have a finite number of predefined production stop states, each of which being pre-classified in one of a plurality of different classes, wherein the evaluation of the cause of the production stop comprises registering the production stop state; and checking the class associated with the registered production stop state, and wherein the automatic preventive cleaning of the non-contact printing unit is initiated when the registered production stop state belongs to one or more predetermined classes.

23. The system according to claim 22, wherein the classes are associated with a gradually increasing estimated time duration for the production stop.

24. The system according to claim 20, further comprising a control system, wherein the control system is arranged for generating a unique alarm signal for each production stop state, each alarm signal being pre-classified in one of a plurality of different classes, wherein the evaluation of the cause of the production stop comprises registering the alarm signal and checking the class associated with the registered alarm signal, and wherein the automatic preventive cleaning of the non-contact printing unit is initiated when the registered alarm signal belongs to one or more predetermined classes.

25. The system according to claim 20, further comprising a control system, wherein the control system is arranged for comprising a cleaning urgency index representing the cleaning urgency of the printing unit, wherein the control system is arranged for monitoring the cleaning urgency index and taking the result of both the production stop evaluation and current cleaning urgency index into account while deciding upon initiating the automatic preventive cleaning of the non-contact printing unit.

26. The system according to claim 25, wherein the cleaning urgency index is a function of one or more of: time period since previous printing unit cleaning event; printing unit still stand time period; ink flow resistance in the printing nozzle; accumulated length of sheet material of the absorbent article having passed the printing unit; and accumulated printing volume.

27. The system according to claim 15, wherein the production stop is an unplanned production stop.

28. The system according to claim 15, wherein the system is arranged for initiating additional automatic cleaning of the non-contact printing unit upon the non-contact printing unit providing an error signal to the production line control system.

* * * * *